(12) United States Patent
Bell et al.

(10) Patent No.: US 11,832,969 B2
(45) Date of Patent: Dec. 5, 2023

(54) MACHINE LEARNING APPROACH TO BEAMFORMING

(71) Applicant: THE JOHNS HOPKINS UNIVERSITY, Baltimore, MD (US)

(72) Inventors: Muyinatu Bell, Towson, MD (US); Austin Reiter, Severna Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 230 days.

(21) Appl. No.: 15/852,106

(22) Filed: Dec. 22, 2017

(65) Prior Publication Data

US 2018/0177461 A1 Jun. 28, 2018

Related U.S. Application Data

(60) Provisional application No. 62/437,941, filed on Dec. 22, 2016.

(51) Int. Cl.
*A61B 5/00* (2006.01)
*A61B 8/08* (2006.01)
(Continued)

(52) U.S. Cl.
CPC .......... *A61B 5/7267* (2013.01); *A61B 5/0095* (2013.01); *A61B 5/7203* (2013.01);
(Continued)

(58) Field of Classification Search
CPC ....... A61B 5/00; A61B 5/0095; A61B 5/7203; A61B 5/7425; A61B 8/5207; A61B 8/463; A61B 8/5269; A61B 2034/2063; A61B 5/7264–7267; A61B 2562/0204; G06N 3/084; G06N 3/08; G06N 3/0454;
(Continued)

(56) References Cited

U.S. PATENT DOCUMENTS

| 4,979,124 A | * | 12/1990 | Sachse | ................. G01N 29/045 706/22 |
| 5,586,200 A | * | 12/1996 | Devaney | ................... G06T 9/20 382/232 |

(Continued)

OTHER PUBLICATIONS

Bradley ["k-Wave: MATLAB toolbox for the simulation and reconstruction of photoacoustic wave fields" Journal of Biomedical Optics 15(2), 021314 (Mar./Apr. 2010)]. (Year: 2010).*

(Continued)

*Primary Examiner* — Oommen Jacob
(74) *Attorney, Agent, or Firm* — JOHNS HOPKINS TECHNOLOGY VENTURES

(57) ABSTRACT

An embodiment according to the present invention includes a method for a machine-learning based approach to the formation of ultrasound and photoacoustic images. The machine-learning approach is used to reduce or remove artifacts to create a new type of high-contrast, high-resolution, artifact-free image. The method of the present invention uses convolutional neural networks (CNNs) to determine target locations to replace the geometry-based beamforming that is currently used. The approach is extendable to any application where beamforming is required, such as radar or seismography.

21 Claims, 13 Drawing Sheets

(51) Int. Cl.
*G06N 3/08* (2023.01)
*A61B 8/00* (2006.01)
*G06T 5/00* (2006.01)
*G06N 3/084* (2023.01)
*G06N 3/045* (2023.01)
*G06N 20/00* (2019.01)
*A61B 34/20* (2016.01)

(52) U.S. Cl.
CPC ............ *A61B 5/7425* (2013.01); *A61B 8/463* (2013.01); *A61B 8/5207* (2013.01); *A61B 8/5269* (2013.01); *G06N 3/045* (2023.01); *G06N 3/08* (2013.01); *G06N 3/084* (2013.01); *G06T 5/002* (2013.01); *A61B 2034/2063* (2016.02); *G06N 20/00* (2019.01); *G06T 2207/10132* (2013.01)

(58) Field of Classification Search
CPC ............... G06N 20/00; G06N 3/00–12; G06N 5/00–04; G06T 5/002; G06T 2207/10132; G06F 19/00–30
See application file for complete search history.

(56) References Cited

U.S. PATENT DOCUMENTS

| | | | | |
|---|---|---|---|---|
| 5,884,294 | A * | 3/1999 | Kadar | G06K 9/6267 382/155 |
| 8,045,805 | B2 | 10/2011 | Ramsay et al. | |
| 8,622,915 | B2 | 1/2014 | Dala-Krishna | |
| 8,725,669 | B1 * | 5/2014 | Fu | A61B 5/726 706/22 |
| 2004/0204645 | A1 * | 10/2004 | Saadat | A61B 5/06 600/117 |
| 2009/0204558 | A1 * | 8/2009 | Weston | G06K 9/6251 706/20 |
| 2012/0035462 | A1 * | 2/2012 | Maurer, Jr. | A61B 6/5247 600/411 |
| 2012/0293843 | A1 * | 11/2012 | Yamakawa | H04N 1/4097 358/448 |
| 2014/0187942 | A1 | 7/2014 | Wang et al. | |
| 2014/0228714 | A1 * | 8/2014 | Chau | A61B 5/1123 600/593 |
| 2015/0272694 | A1 * | 10/2015 | Charles | A61B 90/98 600/202 |
| 2015/0313578 | A1 * | 11/2015 | Yu | A61B 8/463 600/459 |
| 2016/0259898 | A1 * | 9/2016 | Kim | G16H 30/20 |
| 2016/0317118 | A1 | 11/2016 | Parthasarathy et al. | |
| 2016/0317127 | A1 * | 11/2016 | dos Santos Mendonca | A61B 8/5276 |
| 2016/0350620 | A1 | 12/2016 | Rao et al. | |
| 2017/0185871 | A1 * | 6/2017 | Zhang | G06N 3/0454 |
| 2017/0337693 | A1 * | 11/2017 | Baruch | G06T 7/168 |
| 2018/0144466 | A1 * | 5/2018 | Hsieh | G06F 19/00 |

OTHER PUBLICATIONS

Jabbar ["Using Convolutional Neural Network for Edge Detection in Musculoskeletal Ultrasound Images" 2016 International Joint Conference on Neural Networks (IJCNN), Jul. 24-29, 2016] (Year: 2016).*

Chen ["Standard Plane Localization in Fetal Ultrasound via Domain Transferred Deep Neural Networks"} IEEE Journal of Biomedical and Health Informatics, vol. 19, No. 5, Sep. 2015 (Year: 2015).*

Jain ["Natural Image Denoising with Convolutional Networks" Advances in Neural Information Processing Systems 21 (NIPS 2008)] (Year: 2008).*

Yuan ["Feature extraction and image retrieval based on AlexNet", Eighth International Conference on Digital Image Processing (ICDIP 2016),] (Year: 2016).*

Jiao ["A deep feature based frame work for breast masses classification" Neurocomputing197(2016)221-231 (Year: 2016).*

Kahl ["A Neural Network Based Classifier for Ultrasonic Raw Data of the Myocardium", 1997 IEEE Ultrasonics Symposium] (Year: 1997).*

Liu ["Structure noise reduction of ultrasonic signals using artificial neural network adaptive filtering", Ultrasonics 35 (1997) 325-328] (Year: 1997).*

Vicen, Non-linear filtering of ultrasonic signals using neural networks, Ultrasonics 42 (2004) 355-360 (Year: 2004).*

Bettayeb, An improved automated ultrasonic NDE system by wavelet and neuron networks, Ultrasonics 42 (2004) 853-858 (Year: 2004).*

Serrano, A New Method for Object Identification in Ultrasonic Systems Using Neural Nets, 1997 IEEE (Year: 1997).*

Carullo, Ultrasonic Distance Sensor Improvement Using a Two-Level Neural Network, IEEE Transactions on Instrumentation and Measurement, vol. 45, No. 2, Apr. 1996 (Year: 1996).*

Grabec, Application of an intelligent signal processing system to acoustic emission analysis, The Journal of the Acoustical Society of America 85, 1226 (1989) (Year: 1989).*

* cited by examiner

FIG. 2B     FIG. 2C

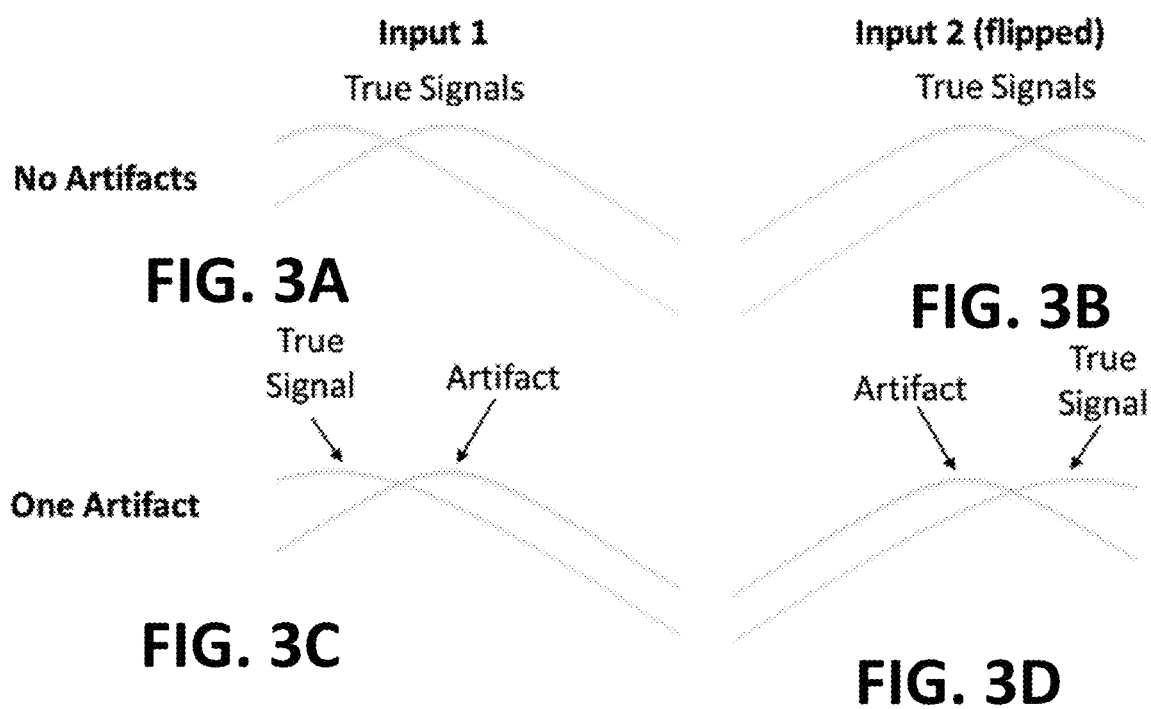

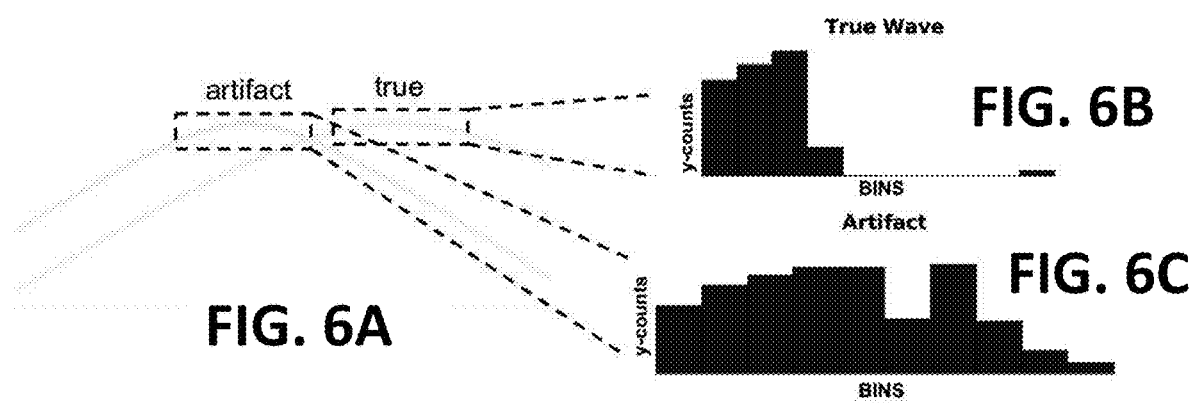

MACHINE LEARNING APPROACH TO BEAMFORMING

CROSS REFERENCE TO RELATED APPLICATIONS

This application claims the benefit of U.S. Provisional Patent Application No. 62/437,941, filed Dec. 22, 2016, which is incorporated by reference herein, in its entirety.

FIELD OF THE INVENTION

The present invention relates generally to imaging. More particularly, the present invention relates to a machine learning approach or alternative to beamforming and image formation.

BACKGROUND OF THE INVENTION

Ultrasound imaging is a long-standing, widely accepted clinical, diagnostic, and surgical guidance tool that has been in existence since the 1950s. However, it is well known that noise artifacts are a severe problem in ultrasound imaging, as they obscure targets of interest, complicate anatomical measurements, and degrade the reliability of image-guided procedures, particularly in overweight and obese individuals, who account for 78.6 million adults and 12.8 million children in North America. Adverse clinical effects of noise artifacts in ultrasound images include poor visibility of 31-50% of fetal anatomical structures and 45-50% of critical cardiac structures. In addition, poor images are the reason for only 49% sensitivity when diagnosing fatty liver disease with ultrasound, although this is the most widely accepted diagnostic approach. Similarly, in interventional and surgical applications that rely on image guidance with ultrasound, the presence of one or more surgical instruments generates imaging artifacts that obfuscate instrument location, orientation, and geometry, while obscuring nearby tissues. These artifacts are reported as significant challenges in intravascular ultrasonography, biopsy guidance, and anesthetic practices.

Photoacoustic imaging is a relatively novel and emerging imaging modality. Proposed for medical applications in the 1990s, it adds a laser to conventional ultrasound technology, utilizing both light and sound to make images (i.e., optical absorption causes rapid thermal expansion and contraction, generating acoustic waves with ultrasonic frequencies that are detected with conventional ultrasound probes). When implementing photoacoustic imaging, strong acoustic reflectors often complicate differentiation of true signals from noise. Due to its novelty, photoacoustic imaging is not yet ubiquitous in the clinic (as is ultrasound), thus the detrimental effects of noise artifacts in these images are not widely reported in literature. However, because both imaging methods use the same existing technology (i.e., acoustic hardware, ultrasound probes, and signal processing methods), it directly follows that similar adverse effects will be prevalent with the rise of clinical applications of photoacoustic imaging—as long as the same historical signal processing techniques are used.

As an example, FIGS. 1A and 1B illustrate two hyperechoic metal photoacoustic targets (i.e., brachytherapy seeds) implanted in an in vivo canine prostate. These seeds are highly visible in the ultrasound image (FIG. 1A), yet cause the reflection artifacts seen in addition to the two seeds in the photoacoustic image (FIG. 1B). These artifacts were not present when only one seed was implanted. Although photoacoustic imaging helps with better identification of the brachytherapy seed locations, the artifact could be mistaken as another photoacoustic target that is not visible in the ultrasound image. This potential confusion is quite common, as ultrasound and photoacoustic images each provide inherently different contrast information (i.e. ultrasound images show differences in acoustic impedance, while photoacoustic images show differences in optical absorption).

The image quality obtained in both ultrasound and photoacoustic images hinges on the quality of the beamforming process, which is a signal processing technique used to convert the acoustic wavefields received by the multiple array elements of an ultrasound probe into a usable image for guiding surgeries and procedures. This process is the first line of software defense against a poor quality image. Historically, typical beamformers have summarized acoustic propagation as a simple time-of-flight measurement to account for signal time of arrival differences. Thus, in ultrasound image reconstruction, the delay function in delay-and-sum beamforming is computed from the distance between transceivers and the target.

The acoustic wave is first transmitted from the ultrasound transducer, through a medium with a specific sound speed and reflected at boundaries with impedance mismatching. The backscattered sound is received by the ultrasound transducer. The ideal acoustic time-of-flight for the ultrasound imaging process, $t_{US}$, can be described mathematically as:

$$t_{US}(r_F) = \frac{1}{c}(|r_t| + |r_r|) \tag{1}$$

where $r_F$ is the focus point originating from the ultrasound image coordinates, $r_t$ is the vector from the transmit element to the focal point, $r_r$ is the vector from the focal point to the receive element, and c is the speed of sound. In clinical ultrasound systems, sequential beamforming with dynamic or fixed focusing is generally applied.

The acoustic time-of-flight for photoacoustic signals, $t_{PA}$, is generally half that of ultrasound, because the acoustic wave is generated at the target by absorbing optical energy, which then travels for reception by the ultrasound transducer (the optical transmission time is negligible). Therefore, the acoustic time-of-flight for photoacoustic imaging is:

$$t_{PA}(r_F) = \frac{|r_r|}{c} \tag{2}$$

FIGS. 1A-1B illustrate ultrasound and photoacoustic images beamformed with conventional delay-and-sum and unconventional coherence-based approaches. Note that Eqs. 1 and 2 do not consider that signals can be reflected multiple times and each acoustic reflection will be measured by the ultrasound transducer, thereby mapping these reverberant signal sources to the wrong location. In principle, there are many paths that an acoustic signal can take once it encounters a strong reflector, which complicates the development of any geometry-based model. Therefore, once these and other geometry-based models are developed and implemented, they are inherently suboptimal in the presence of unexpected reflections. This uncertainty is caused by the multiple variables that determine acoustic wave propagation, such as tissue properties (e.g. speed of sound, attenuation, absorption), tissue type (e.g. fat, bone, muscle), tissue thickness, and refraction.

One research group recently attempted to address the challenge caused by bright reflectors in photoacoustic images by developing an algorithm called photoacoustic-guided focused ultrasound (PAFUSion), which requires acquisition and processing of co-registered ultrasound and photoacoustic data. The ultrasound data is used to identify reflection artifacts by mimicking the wave fields produced by photoacoustic sources. While this method relies on geometry, the advantage with this method depends on the assumption that the acoustic reception geometry for the ultrasound and photoacoustic images are identical. As a result, PAFUSion can only identify and compensate for reflection artifacts caused by PA signals generated inside the imaging plane, and not out-of-plane clutter, causing a significant limitation for interventional applications of photoacoustic imaging. In addition, the requirement for matched ultrasound and photoacoustic images in a real-time environment severely reduces potential frame rates in the presence of tissue motion caused by the beating heart or vessel pulsation. This motion might also introduce error into the artifact correction algorithm.

Two examples of interventional applications where bright reflectors would be a significant impediment to progress and clinical translation, include: (1) the identification of brachytherapy seeds for treating prostate cancer without overdosing healthy tissue and underdosing the cancer, as demonstrated in FIGS. 1A and 1B, and (2) the guidance of minimally invasive neurosurgeries to avoid critical arteries hidden by bone and other tissues.

Deep learning, and more specifically, convolutional neural networks (CNNs), have in recent years redefined the state-of-the-art throughout the computer vision and machine learning communities. Automated capabilities that would not be possible for another 10 years have begun to show promise towards creating intelligent systems that can generalize from training data in remarkable ways. Though CNNs have only recently come to fruition, neural networks date back even further. As they pertain to the proposed work, neural networks were previously used to remove artifacts in ultrasound images by first estimating delay functions based on Eq. 1. These were then used as inputs to a neural network, and the trained network output was delay functions that could be used to remove wavefront distortions, which addresses artifacts caused by false assumptions about the speed of sound. However, this approach would not address the severely problematic reflection artifacts demonstrated in FIG. 1B.

Accordingly, there is a need in the art for a solution or alternative to beamforming that does not rely on traditional geometrical assumptions and instead leverages the capabilities of machine learning.

SUMMARY OF THE INVENTION

The foregoing needs are met, to a great extent, by the present invention which provides a method for removing artifacts in imaging including obtaining pre-beamformed image data. The method includes training a convolutional neural network (CNN). The method further includes inputting the pre-beamformed photoacoustic data into the CNN and outputting a two dimensional point source location for the pre-beamformed image data (if the goal is to detect point sources). Additional target shapes and types could be learned depending on the imaging system's detection task.

In accordance with another aspect of the present invention, the method includes using a non-transitory computer readable medium. The method includes constructing the CNN to receive a raw-pixel image and estimate image formation parameters. The method includes training the CNN through images comprising real, simulated and hybrid images that overlay simulated wavefields onto realistic noisy backgrounds. The method includes customizing the loss function during training to generate simulated images. Additionally, the method includes using a physically based simulator (e.g. k-Wave). The physically based simulator creates images that mimic reality by modeling the physics of an environment. The method includes using k-Wave simulations (or any other acoustic wave simulation package). The method also includes giving the physically based simulator parameters to produce a corresponding image that visualizes a scene based on parameter setting. The method can be applied to photoacoustic and ultrasound image data.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 2A-2C illustrate a schematic diagram of a convolutional neural network trained to relate to pre-beamformed acoustic data to point source locations and graphical views of mean error for axial and lateral position.

FIGS. 3A-3D illustrate graphical views of examples of two point sources in a single pre-beamformed image.

FIGS. 6A-6C illustrate illustrates a schematic diagram of a histogram-based wavefield shape matching technique and graphical views of the true wave and the artifact.

DETAILED DESCRIPTION

Figure 1A:
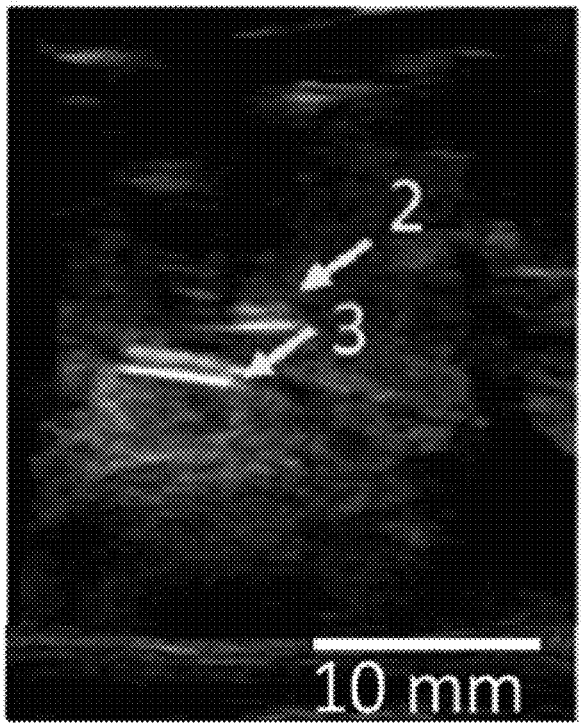
FIGS. 1A and 1B illustrate two hyperechoic metal photoacoustic targets (i.e., brachytherapy seeds) implanted in an in vivo canine prostate.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention includes a method for a machine-learning based approach to the formation of ultrasound and photoacoustic images. The machine-learning approach is used to reduce or eliminate artifacts in the resultant image. The method of the present invention uses convolutional neural networks (CNNs) to determine point source locations to replace the geometry-based beamforming that is currently used. The approach is extendable to any application where beamforming is required, such as radar or seismography.

Given their ability to aid in real-time navigation of complex anatomy, ultrasound and photoacoustic images are popular options for image guidance during surgery. However, noise in these images complicate surgical procedures, particularly noise caused by reflection and reverberation artifacts from highly echogenic structures, which often appear as true signals. If unidentifiable as noise rather than true signals, these artifacts can lead to irreversible damage to surrounding structures such as nerves and major blood vessels, leading to complications such as paralysis and patient death. Currently, none of the widely utilized ultrasound and photoacoustic image formation techniques account for these problematic reflection artifacts, which can arise from multiple factors that are intimately linked, yet difficult to model based on acoustic propagation theories alone. Therefore, the present invention addresses this major engineering challenge in medical ultrasound and photoacoustic imaging by leveraging state-of-the-art machine learning techniques to identify noise artifacts for removal. According to the present invention a convolutional neural network (CNN) using simulated parameters (i.e. axial and lateral point target positions, medium sound speeds, and target radii) is trained to predict realistic image formation parameters directly from raw, pre-beamformed data. The approach of the present invention is both novel and significant because a physically based simulator (i.e. based on the physics of acoustic wave propagation) is embedded directly into the loss function during training of the CNN. Because simulation is incorporated into the loss function, physics can be used to provide ground truth, thereby producing millions of training data with little to no manual curation effort. The present invention will identify and remove reflection artifacts, enhance image quality, and potentially improve surgical success and diagnostic details for millions of patients worldwide. In addition, the approach of the present invention is generalizable to estimate any image formation parameter that can be linked to a simulator.

Figure 1B:
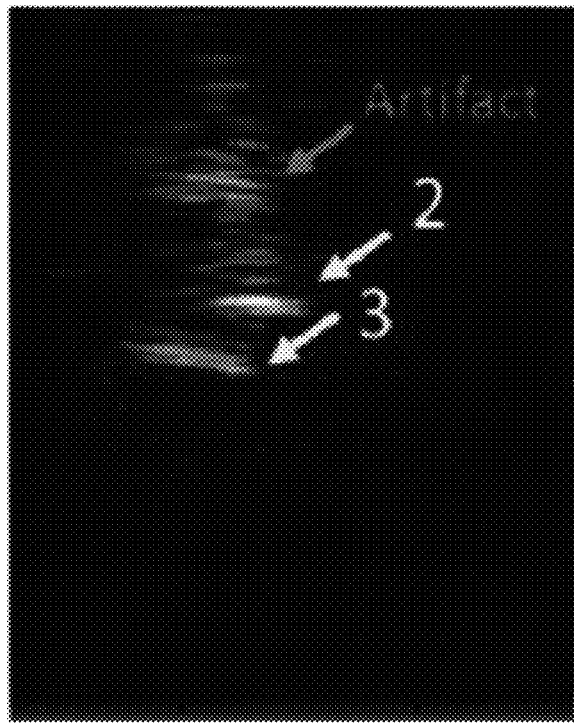
Figure 2A:
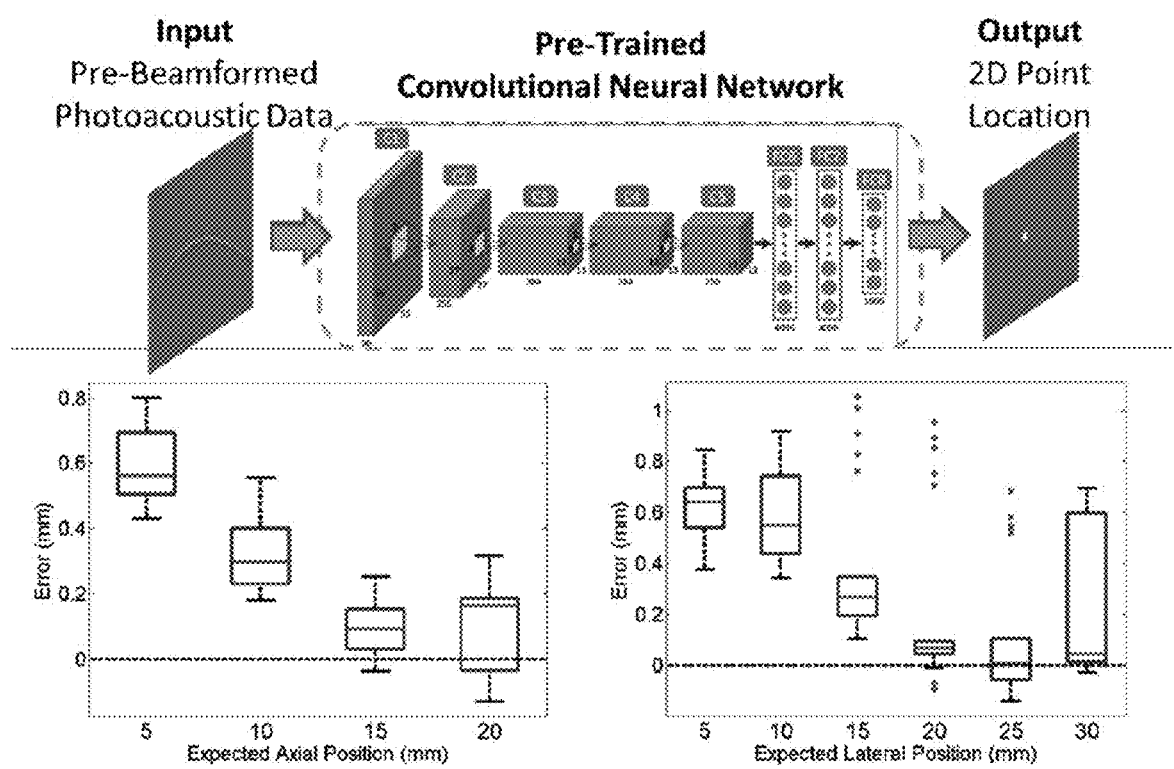

The present invention includes methods to remove the reflection artifacts often seen in interventional photoacoustic imaging (e.g. those shown in FIGS. 1A and 1B) by eliminating geometry-based beamforming and replacing it with a novel approach that uses convolutional neural networks to determine point source locations. An exemplary implementation of the present invention is based on the widely available AlexNet network architecture, where the photoacoustic channel data created with k-Wave simulations was used as the input image. This set-up is not meant to be considered limiting and any suitable implementation of the method of the present invention can be used, as would be known to one of skill in the art. A total of 30,150 input images containing various point locations (axial range: 5-20 mm, lateral range: 5-25 mm), various surrounding medium sound speeds (range: 1440-1640 m/s) causing known errors in the point location, and various point target radii (1-5 mm) were created in simulation. The output of the algorithm contained the point target 2D location in images created under these conditions, as illustrated in FIG. 2A. FIGS. 2A-2C illustrate a schematic diagram of a convolutional neural network trained to relate to pre-beamformed acoustic data to point source locations and graphical views of mean error for axial and lateral position.

The steps taken to achieve the 2D point location included nonlinearity with rectified linear units, max pooling, and regression with L2 normalization. The simulated photoacoustic images were divided into training and test sets. The results of 2,412 test set images revealed that the average point location error was 0.28 mm and 0.37 mm in the axial and lateral dimensions, respectively. The mean errors generally decreased as axial and lateral distance increased as shown in FIGS. 2B and 2C.

Figure 2D:
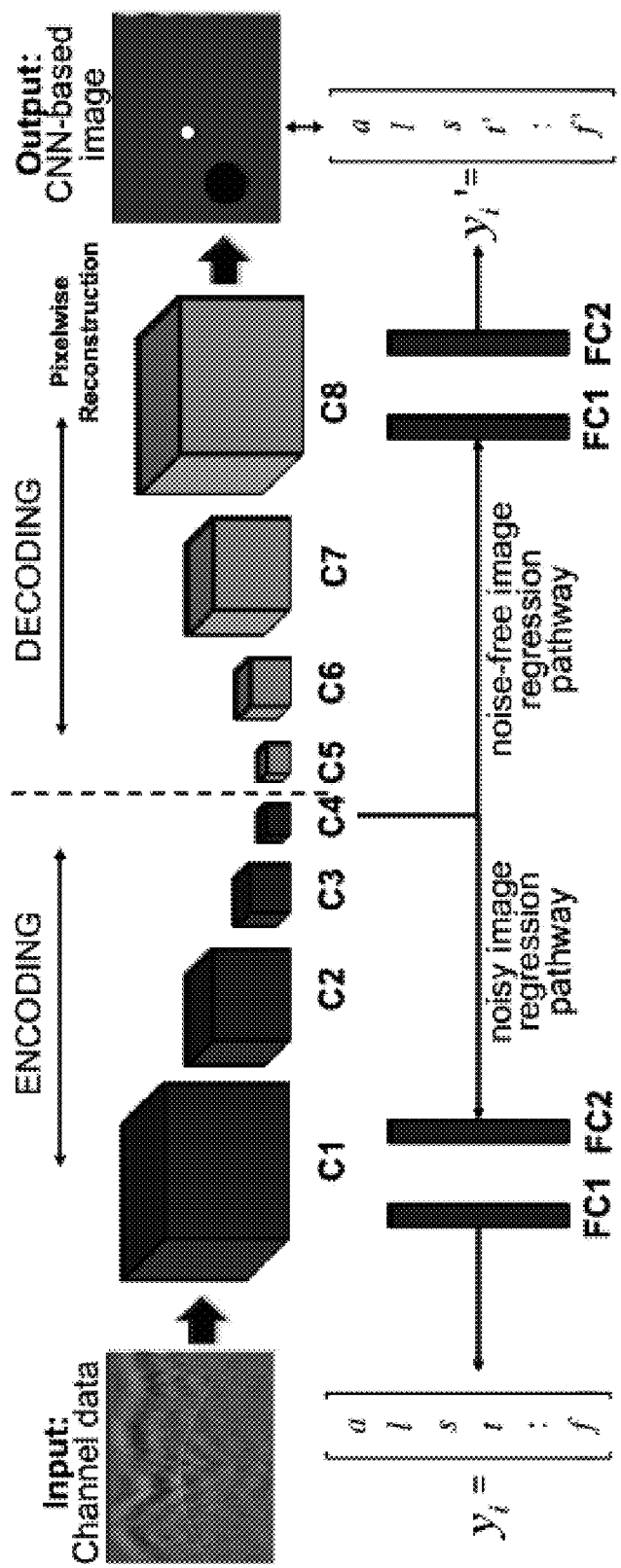
FIG. 2D illustrates a fully convolutional network (FCN), according to an embodiment of the present invention.

FIG. 2D illustrates a fully convolutional network (FCN), according to an embodiment of the present invention. The FCN illustrated in FIG. 2D includes convolutional layers (C1-C8) that are primarily split into "encoding" (left) and "decoding" (right) schemes. The encoding serves to represent raw data input images into a lower-dimensional space, with each successive convolutional layer decreasing the resolution of the parameterization. The decoding then reverses this process to reconstruct images based on examples. The encoding of the FCN will enable branching off to two secondary pathways (bottom of FIG. 2D) and perform regression tasks using the multidimensional parameters described above. Specifically, fully connected layers (FC1-FC4) are attached to the end of the innermost encoding convolutional layer (C4 in FIG. 2D), with the task of regressing the most important multidimensional parameters (e.g., $y'_i = [a, l, s, c, t', \ldots, f']$) needed to create an artifact-free image, where $y'_i$ is obtained for example by setting the near-field tissue thickness to $t'=0$ and replacing it with an anechoic region or alternatively, removing all tissue background and learning the true tool tip location, or by adjusting the fat-to-muscle ratio, f, to a new ratio, f', that causes no acoustic clutter. Through these regression tasks, the minimum number of parameters is determined, $y'_i$, needed to create a noise-free image of a specific target (e.g. a needle location and/or a nearby hypoechic structure). The noisy counterpart to each noise-free image is also regressed to maintain a few initial parameters needed to initialize the simulator and create channel data input images for additional training. This regression step is critical for experimental data when $y_i$ and $y'_i$ are otherwise unknown.

There are three unique advantages to the present invention. First, it can produce a large training dataset using a wave propagation simulation package (e.g. k-Wave). With this large dataset, the difficult manual curation process that is common to many CNN methods is not required. To successfully realize this advantage, the appearance of simulated images must closely match real data, which is possible when incorporating nonlinearity or simulating images based on the full wave equation. The second advantage is the unique ability to extract important information (e.g., point source locations and artifact locations) from complex scenes. Third, the present invention employs network models that have already proven to be highly successful in pixel-level segmentation and complex scenes described only by depth, surface normals, and semantic labels.

Traditional applications of machine learning to imaging tend to operate on the final beamformed image. However, due to failure caused by poor image quality using traditional methods, the new approach of the present invention for ultrasound and photoacoustic image formation operates on pre-beamformed, raw channel data. Machine learning is ideally suited to this approach because of the many variables that influence acoustic wave propagation. Results will be useful for interventional, automated, and robotic tracking tasks.

Because the present invention is directed to a data-driven approach to remove noise artifacts, one additional innovation is to consider expectations for traditional image performance metrics in terms of CNN performance, as summarized below and in Table 1 for point-like targets (e.g., tool tips). A similar approach can be derived for other target types.

TABLE 1

Summary of Performance Metrics

| | Traditional | New CNN-Based Definitions |
|---|---|---|
| Noise | $\sigma_{background}$ | $\propto E_{classification}$ |
| Contrast | $\dfrac{\mu_{target}}{\mu_{background}}$ | $\dfrac{n_s A_{signal} / N_{ROI_s}}{n'_s A_{signal} / N_{ROI_b}}$ |
| CNR | $\dfrac{|\mu_{target} - \mu_{background}|}{\sqrt{\sigma_{target}^2 + \sigma_{background}^2}}$ | $\propto \dfrac{A_{signal}(n_s N_{ROI_b} - n'_s N_{ROI_s})}{E_{classification}}$ |
| SNR | $\dfrac{\mu_{target}}{\sigma_{background}}$ | $\propto \dfrac{n_s A_{signal}}{N_{ROI_s} E_{classification}}$ |
| Resolution | FWHM | $\propto E_{localization}$ |

Noise would ideally not exist if data are correctly encoded. However, if all artifact sources are not correctly encoded, this would manifest as a classification error, as measured signals would incorrectly be displayed as sources rather than artifacts. Because the amplitude of these signals can be arbitrarily set as $A_{signal}$, the magnitude of noise within a region of interest (ROI) would be the chosen amplitude multiplied by the number of incorrect sources that appear in the image, $n'_s$, (i.e., Noise=$n'_s A_{signal}$). The limit to background noise is therefore proportional to the artifact classification error, $E_{classification}$, which is defined as the percentage of pixels corresponding to artifacts that are incorrectly identified as sources after training and testing.

The contrast is defined as the ratio between the mean of the signals, $\mu_s$, and the mean of the background noise, $\mu_{background}$, within selected ROIs. From the expression in Table 1 it is seen that contrast is not dependent on $A_{signal}$ if only detecting point targets. Thus, changing the value of $A_{signal}$ is not expected to affect contrast, which is particularly convenient as the network will be trained to detect surgical tool tips and distinguish them from their surroundings. If same-sized ROIs are used for the signal and background (i.e., $N_{ROI_s} = N_{ROI_b}$), contrast would be equivalent to the ratio of correctly identified signals to incorrectly identified signals (i.e., $n_s/n'_s$), otherwise it is equivalent to the ratio: $(n_s N_{ROI_b})/(n'_s N_{ROI_s})$. It is also possible to obtain infinite contrast if $n'_s$=0, indicating that there is no noise in the image (which is ideal). For cyst-like targets, contrast would depend on displayed signal amplitudes and the number of correct classifications for the target and background.

CNR and SNR are related to the previous two definitions, and they are functions of both $A_{signal}$ and $E_{classification}$. If the background ROI contains low levels of noise (i.e., low values of $E_{classification}$), the CNR and SNR will approach infinity.

Traditionally, ultrasound resolution can be defined as the full-width at half maximum (FWHM) of an imaged point target. Considering that point sources are being detected and their locations displayed, the new resolution can be as small as one pixel if there is only one true point associated with a signal. However, point locations are displayed with a size equal to two standard deviations of the localization accuracy of the training results (because a single high-intensity pixel is typically not distinguishable). Location accuracy is defined by distance errors between known tool locations and locations provided by the network. This definition provides information about the confidence of the locations estimated by the network. The resolution definition for these new CNN-based images is therefore tied to the error with which the location of a point source is detected, $E_{localization}$.

As an example, determining tool tip location within the bounds of the theoretical expectations described above enables the present invention to enhance, display, or overlay this information as a high-contrast, point-like structure in co-registered ultrasound and photoacoustic images (and/or in co-registered MRI and CT images if already available). This display method produces a new kind of high-contrast ultrasound-based image that can be uses to represent the tool tip location. A similar display method may be used for hypoechoic structures (see FIG. 2D output and FIG. 10).

The axial position errors are generally smaller than the corresponding speed of sound errors (1440-1640 m/s, which corresponds to a maximum distance error of 0.6 mm in the axial direction when considering the depth-time relationship of ultrasound and photoacoustic data). The Dice coefficients are additionally greater than 0.9 for cyst-like structures (see FIG. 12). These results suggest that the proposed algorithm of the present invention has excellent potential to detect targets, particularly in the presence of clutter caused by speed of sound errors from multiple tissue layers. Once the network is trained, a target can be located at a frame rate of approximately 60 Hz when running this algorithm on a GPU with 4 GHz processing speed.

The present invention is configured to distinguish true signals from reflection artifacts with the help of deep learning. Therefore, the algorithm needs to successfully predict the location of more than one point source. Feasibility was first tested with two sources present in a single image, where both sources were true signals.

A true signal and a corresponding reflection artifact were then simulated, as demonstrated in FIGS. 3C and 3D. Note that the two wavefronts have different shapes, although they appear at the same depth and should therefore have the same shape, as seen in FIGS. 3A and 3B. This difference occurs because one of the wavefields is caused by a simulated reflection artifact. The approach was used to identify the location of the simulated reflection artifact. Although the network identified the source locations with reasonable accuracy, it was unable to differentiate true signals from artifacts because it was not trained to detect these differences. One approach to differentiate the artifact from the true signal is to feed the identified locations of these two wavefields as inputs into an independent k-Wave simulation, then compare the resulting wavefields to those of the original image. Artifacts may then be rejected based on wavefront shape differences. These results support the proposed approach, and they are the first demonstration of machine learning applied to photoacoustic data visualization.

Figure 4:
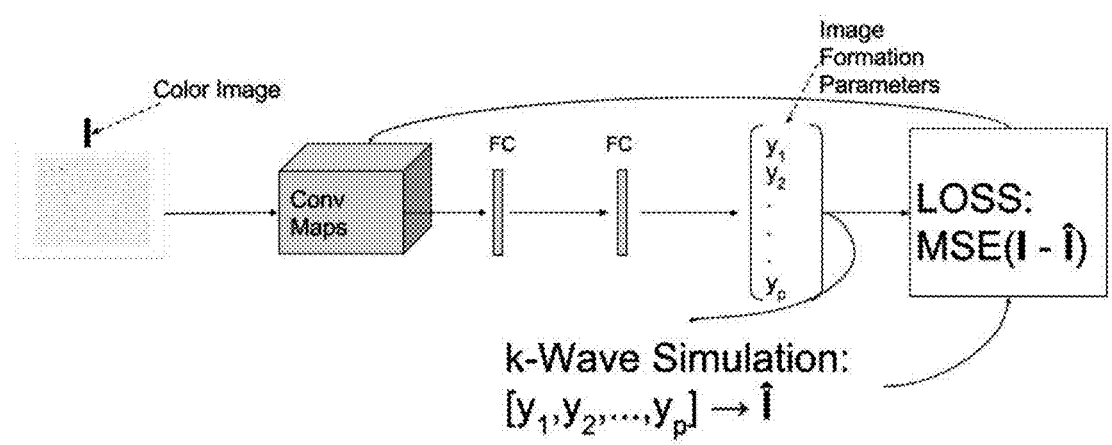
FIG. 4 illustrates a schematic diagram of a proposed algorithm using a physically based simulator.

The results in FIG. 2A and the examples in 3A-3D are shown for one and two point targets. However, there can be an infinite number of point targets in any given image (see FIGS. 7B and 8) and therefore the CNN should be trained to be robust to any situation. In addition, once a wave is detected, a robust method to classify it as either a true signal or an artifact is needed. The primary innovation of the present invention is to estimate the image formation parameters necessary to reproduce an arbitrary input image using a physically-based simulator to guide the training process, as illustrated in FIG. 3D and FIG. 4. FIG. 3D and FIG. 4 illustrate schematic diagrams of proposed algorithms using a physically based simulator. The present invention can also be configured for optimizing the visualization of point-like targets, such as the cross sectional tips of needles, catheters, and other surgical tools, micro-metastases, nanodroplets, breast microcalcifications, and the cross section of small blood vessels.

A Physically-Based Simulator (PBS) is a simulator that is capable of creating images that mimic reality by modeling the physics of a particular environment. For example, this could be photoacoustic data simulated using the same k-Wave simulation software implemented to obtain the results described above. It could also be ultrasound data simulated with the Field II ultrasound simulation package.

The PBS is parameterized through function: $f(y)=\hat{I}$. In plain terms, the simulator is given the parameters y and produces the corresponding image $\hat{I}$ that visualizes the scene based on the parameter setting. Noise artifacts are simulated either by artificially shifting waves to correspond to their appearance in the presence of known bright scatterers, or by using a customized computer program that separately generates these reflection artifacts. The parameters y represent the location and shape of an arbitrary number of point target sources each through an axial (a) and lateral (l) position, medium speed of sound (s), and point target size (t). An arbitrary number of point source targets are supported such that $y=[y_1; y_2, \ldots, y_p]$ for p point source simulated targets. In this case, each $y_i$ (for i=1, \ldots, p) is 4 dimensional: $y_i=[a, l, s, t]$. The reflection artifacts will be labeled separately from the true signal sources based on the known physics of wave propagation.

As shown in FIG. 4, the CNN is constructed to input a raw-pixel image I and estimate the image formation parameters y that best describe the scene portrayed in I. The CNN is trained through a large number of images that may be a combination of real, simulated, and hybrid images that overlay simulated wavefields onto realistic noisy backgrounds. The key to the approach of the present invention is to customize the loss function during training to generate simulated images $\hat{I}$, "on-the-fly", given the predicted PBS parameters y resulting from input image I and compute the mean-squared error of $MSE(I-\hat{I})$. This loss function is then used to update the weights using standard back-propagation with Stochastic Gradient Descent.

There are two advantages to the approach of the present invention. First, a very large training dataset can be produced that would be simple to generate using an off-the-shelf simulator, without a difficult manual curation process that is common to many CNN methods. This means the present invention can utilize both fine-tuning and training from scratch. The second advantage is that the loss function is designed to mimic reality by attempting to reproduce an input image through simulation with physical parameters. In a sense, physics is used to provide ground truth, and this naturally guides the training process. Once converged, the predicted parameters then describe the entire scene, including all point source targets and potential noise artifacts. This is advantageous because arbitrarily complex scenes can be simulated as long as the generated image accurately matches the input image through the predicted image formation parameters.

Point-like sources can be isolated from reflection artifacts with sophisticated, uniquely designed machine learning algorithms that differentiate true signals from signal artifacts using only the raw channel data as an input. If successful, this approach will eliminate the need for traditional geometry-based beamforming (e.g. Eqs. 1 and 2).

The algorithm described herein will initially be developed and evaluated with simulated photoacoustic data, using the same k-Wave simulation software implemented. A total of 500,000-1,000,000 input images will be created containing various point locations (axial range: 5-20 mm, lateral range: 5-25 mm), various surrounding medium sound speeds (range: 1440-1640 m/s), a range of point target radii (1-5 mm), multiple point sources in a single image (2-20), and valid or invalid flags indicating true or reflected wave artifacts. These simulated data will be randomly divided into training and test sets. The error between the predicted and expected point source locations will be recorded. The model is sufficient if the errors are below 1 mm, which is within the resolution of typical photoacoustic imaging systems that utilize low-frequency bandwidth arrays. While these arrays provide poorer resolution compared to their higher frequency counterparts, they are best suited for deep acoustic penetration through tissue, which is a critical requirement for interventional imaging applications. The resolution of this algorithm to accurately determine target size will also be assessed, which will be increasingly important in small surgical workspaces. Determining target size and location will enable display or overlay of this information as a point-like structure in co-registered ultrasound, CT, and/or MRI images, which are common imaging modalities used for image-guided interventions and surgical navigation. Limits for differentiating in-plane and out-of-plane waves will also be explored, as these waves would result in wavefront shape differences, although they may be located at the similar axial depths in a 2D image.

Figure 5:
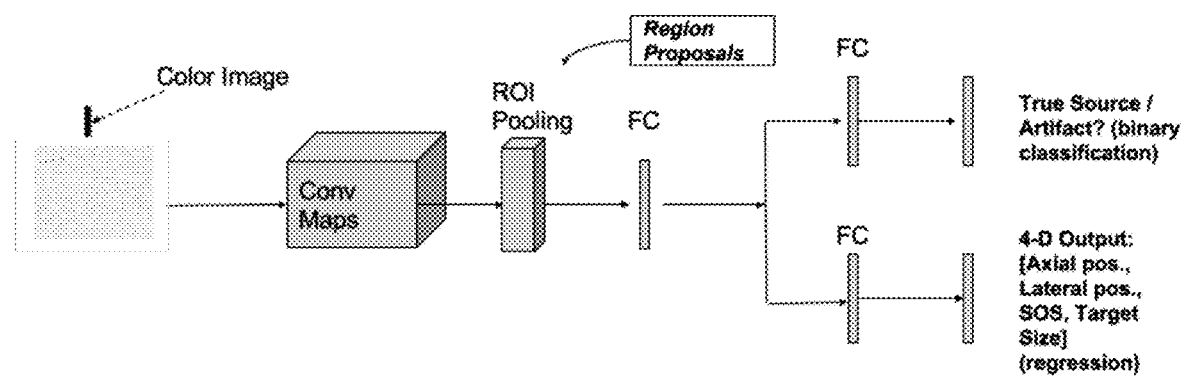
FIG. 5 illustrates a schematic view of a proposed algorithm using more conventional labeling of input data.

Additions to the approaches described herein include valid and invalid flags to differentiate true signals from artifacts, and amplitude differences to determine the relative intensity of each wavefield (which could be important for distinguishing a bright in-plane reflector from a weaker, out-of-plane reflection), as illustrated in FIG. 5. FIG. 5 illustrates a schematic view of a proposed algorithm using more conventional labeling of input data.

FIGS. 6A-6C illustrate a schematic diagram of a histogram-based wavefield shape matching technique and graphical views of the true wave and the artifact. The histogram shows the axial location of the wavefield segments in the dashed boxes. Note the differences in the frequency of the y-coordinates of the wavefield when comparing the histogram for the true wave (FIG. 6B) to that for the artifact (FIG. 6C).

Because the CNN of the present invention will identify the locations of all true and reflected wavefields, this information can be utilized as inputs into an independent k-Wave simulation and compare the resulting wavefields to those of the original image. Finally, sophisticated automated shape-matching methods can be used to accurately distinguish true wavefields from artifacts, as demonstrated by the segmented approach shown in FIG. 6A. This approach is reasonable because artifacts tend to manifest as obviously different wavefield shapes from true signals when they appear at an incorrect depth. To this end, because the CNN can predict these wavefield locations regardless of whether or not they are true or false signals, the shape of the waves at the peak location is then analyzed to construct histograms of the axial positions of the wavefield raw data (i.e. the image y-coordinates), and train a classifier to distinguish amongst these two cases.

Figure 7A:
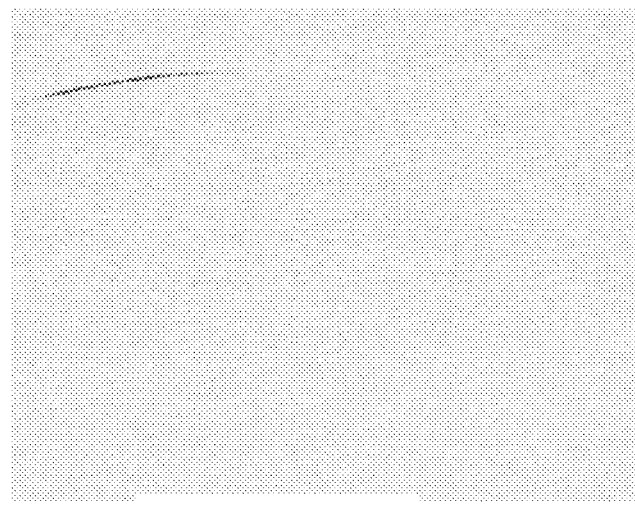
FIGS. 7A-7B illustrate experimental photoacoustic channel data from a 3.8-mm diameter blood vessel phantom, as well as from multiple small blood vessels that generate corresponding noise artifacts when imaging an in vivo finger joint.

FIG. 7A illustrates experimental data from a 3.8 mm diameter blood vessel phantom. One example of the differences between real and simulated data can be appreciated by comparing FIG. 7A with FIGS. 3A-3D; differences include the noisier background, the incomplete wavefield arc, and the nonuniform signal intensities across the wavefield. The axial and lateral positions of the vessel with respect to the ultrasound probe was 6 mm and 11 mm, respectively. The network described herein underestimated these positions by approximately 2 mm in each direction by identifying the locations as 4.21 mm (axial) and 13.01 mm (lateral). This underestimation is within the errors obtained with this network, as shown in FIGS. 2B and 2C, and it demonstrates that the network of the present invention can handle real experimental data.

Figure 7B:
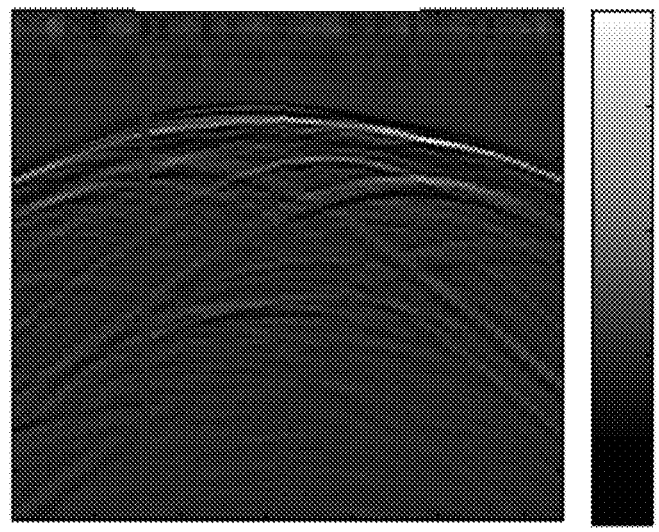

FIG. 7B illustrates experimental data from multiple small blood vessels and corresponding noise artifacts when imaging an in vivo finger joint. FIG. 8B shows another example of the real data containing multiple reflection artifacts. This data is taken from an in vivo finger joint. This finger joint has multiple small vessels that appear point-like in the reconstructed image. One notable difference between this data set and simulated data is the amplitude differences between the various wavefield patterns.

A phantom that contains a needle in ex vivo tissue can be built for testing. This phantom will be used to test cross sectional needle visualization, which should appear point-like in reconstructed images. As a final verification, the example from FIGS. 1A and 1B (and other real in vivo data like it) will be tested to determine if the known artifact can be differentiated from true signals. Although the image shows the longitudinal view of the seeds, which appear more like a line rather than a point, a circular cross-sectional image of two closely spaced 5 mm diameter brachytherapy seeds will be tested. These images will contain the point-like targets that the algorithm of the present invention will be trained to handle, as well as reflection artifacts from the closely spaced seeds. The resulting image can be compared to the beamformed B-mode image to determine if the artifacts were removed.

Figure 8:
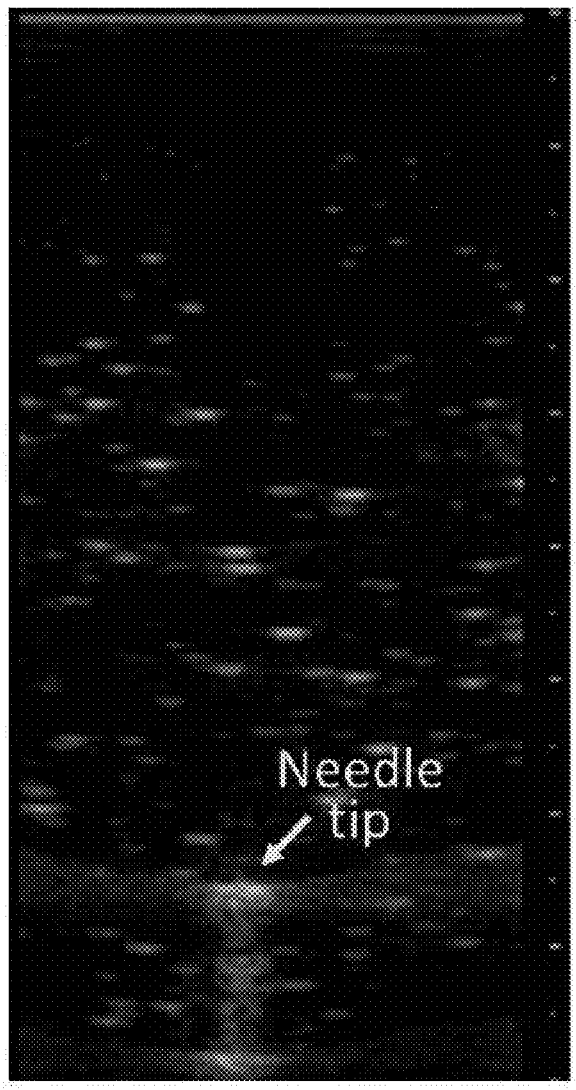
FIG. 8 illustrates an image view of experimental image of microbubbles injected into a water tank through a needle, demonstrating a use case for detecting point-like targets.

Although the examples in FIGS. 7A and 7B are presented for photoacoustic images, the same network can be extended to remove reflection artifacts in ultrasound imaging, because the acoustic reception time of flight for ultrasound signals is the same as that of photoacoustic signals. Making the assumption that each subresolution scatterer in ultrasound data is a point source, the trained network is used to test this assumption with ultrasound data. This assumption is true for biological tissues as well as for microbubbles. FIG. 8 shows an example of the ultrasound image obtained from multiple microbubbles injected through a needle after a plane wave transmission. Notice that each microbubble appears as a point-like target. FIG. 8 illustrates an image view of microbubbles injected into a water tank through a needle.

These microbubble data will be processed with the algorithm developed for Aim 1 to determine the feasibility of detecting multiple point targets when there are no reflection artifacts. The resulting image can be compared to the beamformed B-mode image shown in FIG. 8.

While the microbubbles provide a clever experimental testbed to aid in evaluating the algorithm for ultrasound data, the present invention is ultimately concerned with detecting and removing reflection artifacts in interventional ultrasound images. Therefore, the phantom developed herein for photoacoustic imaging (i.e. a needle in ex vivo tissue) will be imaged with conventional ultrasound techniques. The raw ultrasound channel data will be acquired, and the proposed design will be repeated by imaging this phantom in the absence and presence of the strong needle reflector. This data set is similarly expected to have multiple wavefields with the number of detected points being greater when the strong needle reflector is introduced into the imaging environment. B-mode images without the reflector are compared to B-mode images obtained with the reflection artifact identified and removed after applying the machine learning-based algorithms of the present invention.

These two data sets (microbubbles and ex vivo tissue imaged in the absence and presence of a strong needle reflector) represent two of the most challenging cases for the differentiation of true signals from reflection artifacts in ultrasound data. Successful completion of these experiments to identify true signal locations and remove reflection artifacts will be the ultimate benchmark for the success of the algorithm of the present invention.

Figure 9A:
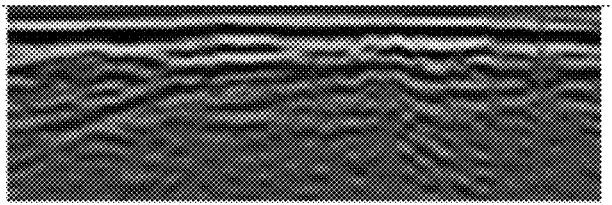
FIGS. 9A and 9B illustrate experimental images of acoustic waves acquired in the absence and presence of ribs from the chest wall.
Figure 9B:
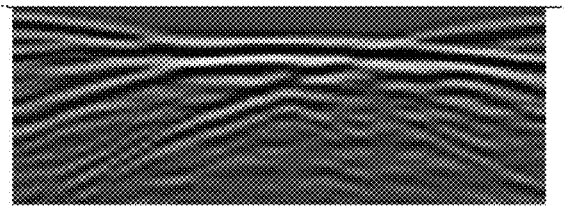

FIGS. 9A and 9B illustrate experimental images of acoustic waves acquired in the absence and presence of ribs from the chest wall. The reflection artifacts from the ribs distort the appearance of the recorded acoustic wavefield. If the k-Wave-trained network does not yield the same accuracy for ultrasound data as achieved for photoacoustic data, due to factors such as sound attenuation differences between ultrasound and photoacoustic data, then a new network can be trained with simulated ultrasound. This training phase with the PBS will utilize the Field II simulation package (which was designed specifically for ultrasound data simulations). The simulation parameters are initially the same as those used for the k-Wave simulations (i.e., axial (a) and lateral (l) position, medium speed of sound (s), and point target size (t)) for an arbitrary number of point sources. With this simulation package the acoustic wavefields from non-point-like sources can also be modeled, such as cysts, tumors, and blood vessels, and thereby build a trained neural network that is not susceptible to reflection artifacts, off-axis scatterers, and inherent thermal noise in the imaging system—the three primary sources of noise artifacts in ultrasound imaging. These artifacts are additional to the reverberation and reflection artifacts that are seen with surgical tools, thus they add an additional layer of complexity to ultrasound signal detection. As an example of this complexity, the acoustic wavefield from one ultrasound transmit and reception event when imaging tissue with and without the chest wall in the ultrasound beam propagation path is shown in FIGS. 9A and 9B. Note the differences in wavefield appearances when ribs from the chest wall are present in the acoustic propagation pathway. The source of each wavefront is to be identified with the innovation described herein.

A wide array of clinical, surgical, and interventional applications can benefit from noise reduction in ultrasound imaging. Similarly, the emerging field of photoacoustic imaging will directly benefit from any advances in ultrasound signal processing. The present invention advances these areas of study by training a model to learn the subtle variations in acoustic wave propagation to avoid incorrect or inaccurate assumptions about acoustic wave propagation. These subtle differences are well suited to developing a model based on machine learning principles. By showing the model several thousand possible cases of wave propagation both in the image plane and outside of the image place plane, there will be significant improvements in terms of noise reduction, resolution enhancement, and target localization.

Figure 10:
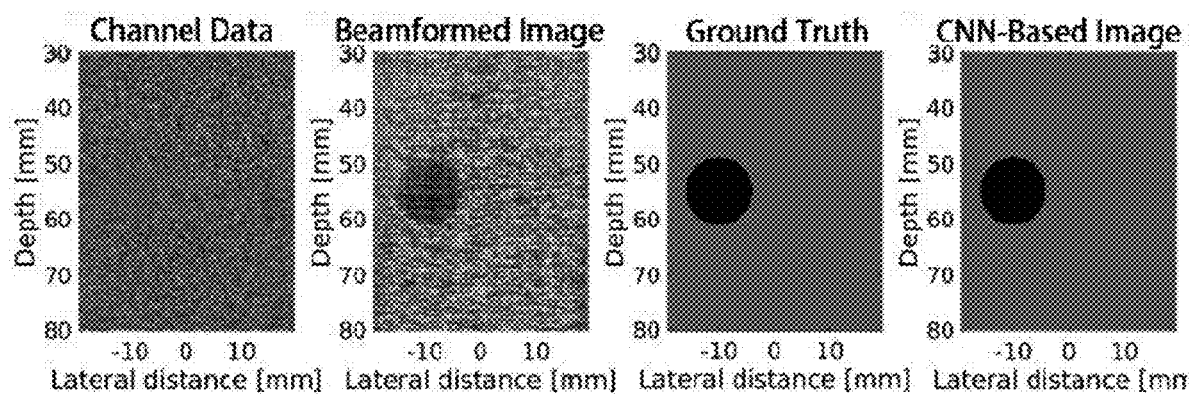
FIG. 10 illustrates graphical views of an ultrasound simulation result along with a ground truth and CNN-based image.

In an alternative embodiment, the CNN can take the form of an FCN without the critical FCs in FIG. 2D, and it was applied to ultrasound data. RF channel data corresponding to various anechoic cyst locations (axial range: −15 to 15 mm, lateral: 35-75 mm) and sizes (radii: 2-8 mm) surrounded by tissue with various sound speeds (1440-1640 m/s), was simulated yielding a total of 32,487 input images. These images were randomly split into training (80%) and testing/validation (20%). FIG. 10 illustrates graphical views of an ultrasound simulation result. The example result in FIG. 10 was obtained from an anechoic cyst after one plane wave ultrasound transmit and reception event. The cyst contrast in the conventional beamformed ultrasound image is 10.15 dB, while that of the CNN-based image is 33.77 dB (a 23.6 dB improvement). The Dice similarity coefficient (DSC) between the CNN image and ground truth is 0.99. FIG. 10 also shows that the FCN works on plane wave ultrasound data with Dice similarity coefficients greater than 0.9 (i.e., over 90% overlap with ground truth).

Figure 11:
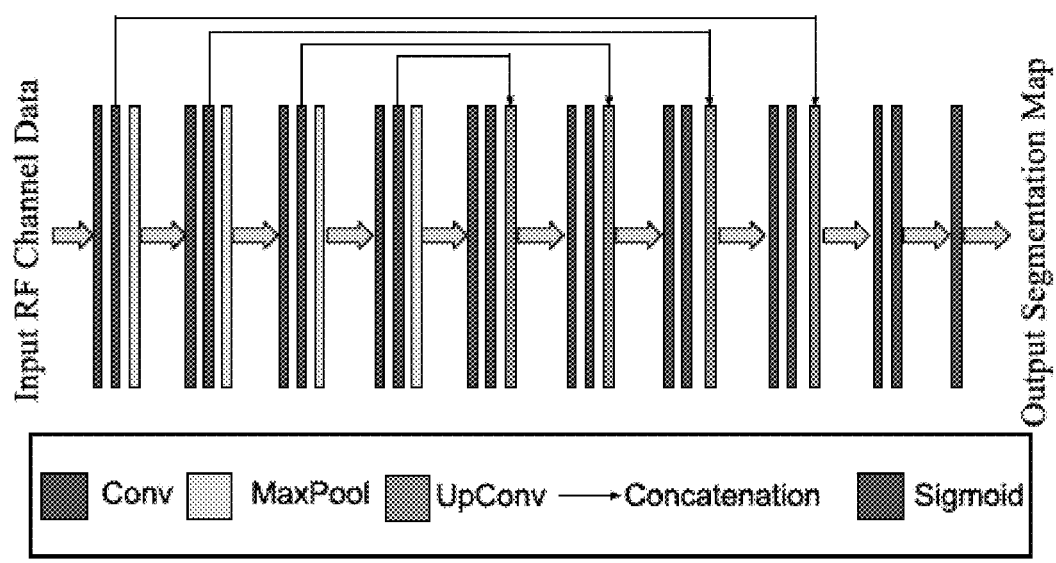
FIG. 11 illustrates a schematic diagram of a fully convolutional encoder-decoder architecture with skip connections for ultrasound image segmentation.

An exemplary implementation of the present invention demonstrates the feasibility of employing deep learning as an alternative to traditional ultrasound image formation and beamforming. The neural network architecture of this exemplary implementation is based on the widely used U-Net segmentation network. FIG. 11 illustrates a schematic diagram of a fully convolutional encoder-decoder architecture with skip connections for ultrasound image segmentation. The architecture, as seen from FIG. 11, is fully convolutional and has two major parts—a contracting encoder path and an expanding decoder path. In the contracting encoder, there are convolutional (Cony) layers and max pooling (MaxPool) layers. For each convolutional (Cony) layer, there are 3×3 convolutions with a stride of 1, and zero padding of the input in order to ensure the sizes of the input and output match. Rectified linear units (ReLU) are used as the non-linearity in the Conv layers. For the max-pooling layers, a pool size of 2×2 is used with stride set to 2 in each direction as well. Each max pool layer thus has an output size half that of the input (hence the term 'contracting'). To offset this, the number of feature channels learned is increased by 2 after every max pooling step.

In the expanding decoder, there are up-convolutional (UpConv) layers, also termed transposed convolutions in addition to regular convolutional layers. The UpConv layers reverse the reduction in size caused by the convolution and max pooling layers in the encoder by learning a mapping to an output size twice the size of the input. As a consequence, the number of feature channels learned in the output are halved. The output of each UpConv layer is then concatenated with the features generated by the segment of the encoder corresponding to the same scale, before being passed to the next part of the decoder. The reason for this is two-fold: to explicitly make the network consider fine details at that scale that might have been lost during the down sampling process, and to allow the gradient to backpropagate more easily through the network through these 'skip' or 'residual' connections, reducing training time and training data requirements.

The final layer of the network is a 1×1 convolutional layer with a sigmoid non-linear function. The output is a per-pixel confidence value of whether the pixel corresponds to the cyst region (predict 1) or tissue region (predict 0) based on the learned multi-scale features. The network is trained end-to-end, using the negative of a differentiable formulation of the Dice similarity coefficient (Eq. 3) as the training loss.

$$\text{Dice}(X, Y) = \frac{2|X \cap Y|}{|X| + |Y|} \quad (3)$$

where X corresponds to vectorized predicted segmentation mask and Y corresponds to the vectorized ground truth mask.

In order to train the network, a large dataset is simulated using the open-source Field II ultrasound simulation software. All simulations considered a single, water-filled anechoic cyst in normal tissue with the region of interest maintained between −19.2 mm and +19.2 mm in the lateral direction and between 30 mm and 80 mm in the axial direction. The transducer was modeled after an Alpinion L3-8 linear array transducer with parameters provided in Table 2. FIG. 10 illustrates an example of RF channel data that is typically beamformed to obtain a readable ultrasound image. A ground truth mask of the anechoic cyst location is compared to the the mask predicted by the neural network. The network provides a clearer view of the cyst location when compared to the conventional ultrasound image created with a single plane wave transmission. The transducer parameters are provided in Table 2.

TABLE 2

Ultrasound transducer parameters

| Parameter | Value |
| --- | --- |
| Element number | 128 |
| Pitch | 0.3 mm |
| Aperture | 38.4 mm |
| Element width | 0.24 mm |
| Transmit Frequency | 8 MHz |
| Sampling Frequency | 40 MHz |

Plane wave imaging was implemented with a single insonification angle of 0°. RF channel data corresponding to a total of 21 different sound speeds (1440 m/s to 1640 m/s in increments of 10 m/s), 7 cyst radii (2 mm to 8 mm in increments of 1 mm), 13 lateral positions (15 mm to 15 mm in steps of 2.5 mm) for the cyst center, and 17 axial locations (35 mm to 75 mm in steps of 2.5 mm) for the cyst center were considered, yielding a total of 32,487 simulated RF channel data inputs after 10,000 machine hours on a high performance cluster. Then an 80:20 split was performed on this data, retaining 25,989 images as training data and using the remaining 6,498 as testing data. The training data was further augmented by flipping it laterally to simulate imaging the same regions with the probe flipped laterally. The original channel data was resized from an initial dimensionality of 2440*128 to 256*128 in order to fit it in memory, and normalized by the maximum absolute value to restrict the amplitude range from −1 to +1.

All neural network code was written in the Keras API on top of a TensorFlow backend. The network was trained for 20 epochs using the Adam optimizer with a learning rate of 1 e$^{-5}$ on negative Dice loss (Eq. 1). Weights of all neurons in the network were initialized using the Glorot uniform initialization scheme. Mini-batch size was chosen to be 16 samples to attain a good trade-off between memory requirements and convergence speed. The training of the neural network was performed on an NVIDIA Tesla P40 GPU with 24 GB of memory.

As visible from FIG. 10, deep learning enables a new kind of ultrasound image—one that does not depend on the classical method of beamforming. Using a fully convolutional encoder-decoder architecture, details are extracted directly from the non-human-readable RF channel data and produce a segmentation mask for the region of interest. This also allows the present invention to overcome common challenges with ultrasound, like the presence of acoustic clutter when using a single insonification angle in plane wave imaging. The presence of speckle is also ignored, which provides better object detectability, although this feature can be considered a limitation for techniques that rely on the presence of speckle.

As a consequence, the final output image is more interpretable than the corresponding beamformed image created with a single plane wave insonification. In addition to requiring less time to create this image, thereby increasing possible real-time frame rates, this display method would require less expert training to understand. The present invention can also serve as supplemental information to experts in the case of difficult-to-discern tissue features in traditional beamformed ultrasound images. In addition, it can also be employed as part of a real-time fully automated robotic tracking system.

Figure 12:
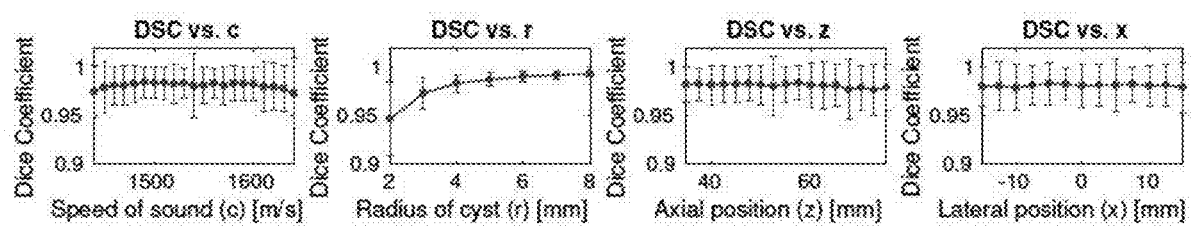
FIG. 12 illustrates graphical views of performance variations of the trained network versus different simulation conditions.

To objectively assess the performance of the neural network of the exemplary implementation, four evaluation criteria are used: 1. Dice score—This is the loss metric that was used to train the neural network as described by Eq. 3. The mean Dice scores for the test data samples was evaluated to be a promisingly high value of 0.9815±one standard deviation of 0.0222. FIG. 12 illustrates graphical views of performance variations of the trained network versus different simulation conditions. Cyst radius (r), speed of sound (c), axial position of cyst center (z), and lateral position of cyst center (x), are varied, aggregating over all other parameters, and the mean Dice similarity coefficient (DSC) is calculated. The error bars show one standard deviation. Contrast is a common measure of image quality, particularly when imaging cysts. It measures the signal intensity ratio between two tissues of interest, here, between that of the cyst and the tissue:

$$\text{Contrast} = 20\log_{10}\left(\frac{S_o}{S_i}\right)$$

where $S_i$ and $S_o$ are the mean signal intensities inside and outside the cyst, respectively. This measurement provides quantitative insight into how discernible the cyst is from its surroundings. A major advantage of the approach of the present invention to image formation is that segmentation into cyst and non-cyst regions is produced with high confidence, which translates to very high contrast. For the example images shown in FIG. 10, the cyst contrast in the conventionally beamformed ultrasound image is 10.15 dB, while that of the image obtained from the network outputs is 33.77 dB, which translates to a 23.62 dB improvement in contrast for this example. Overall, the average contrast for network outputs was evaluated to be 45.85 dB (when excluding results with infinite contrast due to all pixels being correctly classified).

Recall, also known as specificity, is the fraction of positive examples that are correctly labeled as positive. For the network of the exemplary implementation, a test example is defined as correctly labeled if at least 75% of the cyst pixels were correctly labeled as belonging to a cyst. The network yields a recall of 0.9977. This metric indicates that clinicians (and potentiality robots) will accurately detect at least 75% of cyst over 99% of the time.

The time it takes to display the DNN-based images is related to the ability to increase the realtime capabilities of plane wave imaging. The 6,498 test images were processed in 53 seconds using the DNN, which translates to a frame rate of approximately 122.6 frames/s on the single-threaded CPU. Using the same data and computer, conventional beamforming took 3.4 hours, which translates to a frame rate of approximately 0.5 frames/s. When plane wave imaging is implemented on commercial scanners with custom computing hardware, the frame rates are more like 350 frames/s for 40 insonification angles. However, only one insonification angle is being used, which indicates that the approach of the present invention can reduce the acquisition time for plane wave imaging and still achieve real time frame rates while enhancing contrast.

The Dice coefficient produced by the network was evaluated as functions of four simulation parameters: cyst radius (r), speed of sound (c), axial position of cyst center (z), and lateral position of cyst center (x). The average Dice coefficients when fixing the parameter of interest and averaging over all other parameters were calculated. The results are shown in FIG. 12. In each case, the mean Dice coefficients was always greater than 0.94, regardless of variations in the four simulated parameters. Variations in Dice coefficients were most sensitive to cyst size. The Dice coefficients were lower for smaller cysts, with performance monotonically increasing as cyst size increased. This increase with size is likely a result of smaller cysts activating fewer neurons that the network can aggregate for a prediction, and also mirrors traditional ultrasound imaging, where cysts of smaller size are more difficult to discern. Otherwise, the network appears to be more robust to changes in sound speed and the axial and lateral positions of the anechoic cyst.

In addition to being applicable to ultrasound, the method of the present invention can also be applied to photoacoustic imaging. Another exemplary implementation of the present invention demonstrates the first use of convolutional neural networks as an alternative to traditional model-based photoacoustic beamforming techniques. It also demonstrates that classification accuracy is sufficient to differentiate sources from artifacts when the background noise is sufficiently low. Training requires incorporation of all potential source locations to maximize classification accuracy networks were trained with simulated data, yet performed reasonably well when transferred to experimental data. The CNN-based artifact removal method results in a noise-free, high contrast, high resolution image that can be used as a mask or scaling factor for beamformed images, or it could serve as a stand-alone image.

A deep neural network can be applied to learn spatial impulse responses and locate photoacoustic signals with an average positional accuracy of 0.28 mm and 0.37 mm in the depth and lateral image dimensions, respectively. This exemplary implementation includes a deep neural network capable of locating both sources and artifacts in the raw photoacoustic channel data with the goal of removing the artifact from the image. Second, this exemplary implementation includes the potential for artifact replacement based on the information provided by the CNN.

In the exemplary application to photoacoustic imaging the neural networks were trained using source and artifact locations at 5 mm increments, thus in order to test how well the trained networks adapted to signal locations that were not encountered during training, three additional noiseless datasets were created by: (1) shifting the initial lateral positions by 2.5 mm to the right while keeping the initial depth spacing, (2) shifting the initial depth positions by 2.5 mm while keeping the initial lateral spacing, and (3) shifting the initial lateral. Building on the initial simulations, which were tailored to clinical scenarios with a high probability of structures appearing at discrete 5 mm spacings (e.g., photoacoustic imaging of brachytherapy seeds), a new set of simulated point sources was generated with more finely spaced points. The depth and lateral increment was reduced from 5 mm to 0.25 mm. While the initial dataset contained 1,080 sources, this new dataset contained 278,154 sources. Because of this large number of sources, point target locations were randomly selected from all possible source locations, while artifact locations were randomly selected from all possible points located less than 10 mm from the source. A total of 19,992 noiseless channel data images were synthesized for each dataset, and a new network was trained (80% of images) and tested (20% of images) for each dataset.

In generating reflection artifacts, two different methods were compared. In the first, the artifact wavefront was shifted 5 mm deeper into this image. This 5 mm distance was chosen because it corresponds to the spacing of brachytherapy seeds, which motivate this work. In the second method, the shift was more precisely calculated to equal to the Euclidean distance, $\Delta$, between the source and artifact, as described by the equation:

$$|\Delta|=\sqrt{(z_s-z_r)^2+(x_s-x_r)^2}$$

where $(x_s, z_s)$ are the 2D spatial coordinates of the source location and $(x_r, z_r)$ are the 2D spatial coordinates of the physical reflector location. To compare the two methods, two noiseless, finely-spaced networks were trained, one for each shifting method.

In simulating photoacoustic channel data, two different sampling schemes are compared. In the first the transducer is modeled as a continuous array of elements whose sampling rate is dependent on the speed of sound in the medium, this is the default k-Wave behavior in determining sampling frequency. In the second model, the transducer being used is explicitly modeled.

Two changes were made in order to mimic a transducer, the first was modeling the transducer elements not as a continuous array but modeling discrete elements with spacing between them.

One method of artifact removal is to use the network outputs to display only the locations of the detected source signals in the image. Source detections can be visualized as circles centered at the center of the detection bounding box with a radius corresponding to $2\sigma$, where $\sigma$ is the standard deviation of location errors found when testing the network.

The present invention can also be applied to networks with 1 source and multiple artifacts when transferred to experimental data. Alternately, the network works with multiple sources. Modeling the ultrasound transducer improves accuracy when transferring simulation-trained results to experimental data.

The steps and analysis of the present invention can be carried out using a smartphone, a tablet, internet or cellular enabled device, computer, non-transitory computer readable medium, or alternately a computing device or non-transitory computer readable medium incorporated into the imaging device. Indeed, any suitable method of calculation known to or conceivable by one of skill in the art could be used. It should also be noted that while specific equations are detailed herein, variations on these equations can also be derived, and this application includes any such equation known to or conceivable by one of skill in the art. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computing device designed specifically for this purpose. The computing device can be unique to the present invention and designed specifically to carry out the method of the present invention. The computing device can also be directly incorporated into a scanner, ultrasound, or other imaging device associated with the present invention.

The many features and advantages of the invention are apparent from the detailed specification, and thus, it is intended by the appended claims to cover all such features and advantages of the invention, which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for removing artifacts comprising:
   obtaining ultrasonic or photoacoustic channel or sensor data received from a plurality of ultrasound transducer elements, wherein the ultrasonic or photoacoustic channel or sensor data has not been beamformed;
   applying a convolutional neural network (CNN), wherein the CNN is configured for:
   identifying and distinguishing true signals from reflection artifacts in the ultrasonic or photoacoustic channel or sensor data and removing the reflection artifacts from the raw ultrasonic or photoacoustic channel or sensor data;
   inputting the ultrasonic or photoacoustic channel or sensor data into the CNN, wherein the CNN is configured to decrease resolution of the ultrasonic or photoacoustic channel or sensor data;
   wherein the CNN is configured for reconstruction to generate a revised set of ultrasonic or photoacoustic channel or sensor data wherein the reflection artifacts are removed; and,
   outputting an image view from the revised set of ultrasonic or photoacoustic channel or sensor data.

2. The method of claim 1 further comprising executing the method using a non-transitory computer readable medium.

3. The method of claim 1 further comprising constructing the CNN to receive the ultrasonic or photoacoustic channel or sensor data in the form of a raw-pixel image and estimate image formation parameters, wherein image formation parameters comprise one selected from a group consisting of point source location, point source size, target size, or medium sound speed.

4. The method of claim 1 further comprising training the CNN through data from images comprising real, simulated and hybrid images that overlay simulated data onto realistic noisy backgrounds.

5. The method of claim 1 further comprising customizing a loss function during training to generate simulated images.

6. The method of claim 1 further comprising using a physically based simulator.

7. The method of claim 6 further comprising using the physically based simulator to create images that mimic reality by modeling the physics of an environment.

8. The method of claim 6 further comprising using one or more of a k-Wave, Field II, or full wave simulation.

9. The method of claim 6 further comprising giving the physically based simulator parameters to produce a corresponding image that visualizes a scene based on parameter setting.

10. The method of claim 9 further comprising using the method for ultrasound image data.

11. The method of claim 3 that overlays the image view onto a traditional beamformed image.

12. The method of claim 3 that displays the image view as a separate image.

13. The method of claim 1 wherein the ultrasound or photoacoustic channel or sensor data includes extracting details directly from non-human-readable channel data and producing a segmentation mask.

14. The method of claim 1 further comprising tracking a target in the image view, wherein the tracking can be performed with or without a robotic system.

15. The method of claim 1 further comprising locating both point sources and artifacts in the ultrasound or photoacoustic channel or sensor data to remove the artifact from an image.

16. The method of claim 1 further comprising tracking a surgical tool that generates artifacts in the image view.

17. The method of claim 1 further comprising simulating image targets by replacing pixels inside a detection bounding box in channel data with a per-pixel confidence value of the image view.

18. The method of claim 1 further comprising simulating image target locations by replacing pixels inside a detection bounding box in channel data with a per-pixel confidence value of a noise level of the image view.

19. The method of claim 1 further comprising using network outputs to display only locations of detected source signals in the image view.

20. The method of claim 1 further comprising modeling an ultrasound transducer used in obtaining the ultrasound or photoacoustic channel or sensor data.

21. The method of claim 1 further comprising creating images by replacing identified pixels in channel data corresponding to noise regions.

* * * * *